United States Patent [19]

Clement et al.

[11] Patent Number: 4,737,151
[45] Date of Patent: Apr. 12, 1988

[54] SYRINGE INJECTOR

[76] Inventors: John G. Clement, 6011 Wiltshire Street, Vancouver, British Columbia, Canada, V6M 3L8; David R. Harker, 19881 - 35th Avenue, Langley, British Columbia, Canada, V3A 2P7

[21] Appl. No.: 889,212

[22] Filed: Jul. 25, 1986

[51] Int. Cl.[4] .......................... A61M 1/00; A61M 5/00
[52] U.S. Cl. ................................... 604/223; 222/327; 604/181; 128/DIG. 12
[58] Field of Search ............... 604/207, 208, 407, 223, 604/224, 181, 184, 62, 152, 154, 97, 225; 222/327 OR, 327; 30/120.5; D7/98; 128/DIG. 12

[56] References Cited

U.S. PATENT DOCUMENTS

| | | | |
|---|---|---|---|
| 3,063,449 | 11/1962 | Schultz | 604/181 |
| 3,311,143 | 3/1967 | Vetter | D7/98 |
| 3,578,047 | 5/1971 | Diggs | D7/98 |
| 3,905,365 | 9/1975 | Colombo | 604/223 |
| 4,067,334 | 1/1978 | Haller | 604/223 |
| 4,090,639 | 5/1978 | Campbell et al. | 604/223 |
| 4,132,231 | 1/1979 | Puccio | 128/DIG. 12 |
| 4,198,975 | 4/1980 | Haller | 604/223 |
| 4,255,855 | 3/1981 | Brazil | 30/120.5 |
| 4,544,369 | 10/1985 | Skakoon | 128/DIG. 12 |
| 4,620,848 | 11/1986 | Sutherland | 128/DIG. 12 |
| 4,659,326 | 4/1987 | Johnson et al. | 604/62 |

Primary Examiner—C. Fred Rosenbaum
Assistant Examiner—Sharon Rose
Attorney, Agent, or Firm—Beehler, Pavitt, Siegemund, Jagger, Martella & Dawes

[57] ABSTRACT

A syringe injector to hold a syringe that comprises a barrel and a plunger. The plunger includes a piston received in the barrel. The injector comprises a support frame with a cradle to receive the syringe barrel at one end of the support frame. The plunger is held and there is a lever pivotally attached to the frame. A connecting rod extends from the lever to the holding means. In use, movement of the lever moves the plunger of the syringe and affords mechanical advantage to the user.

11 Claims, 3 Drawing Sheets

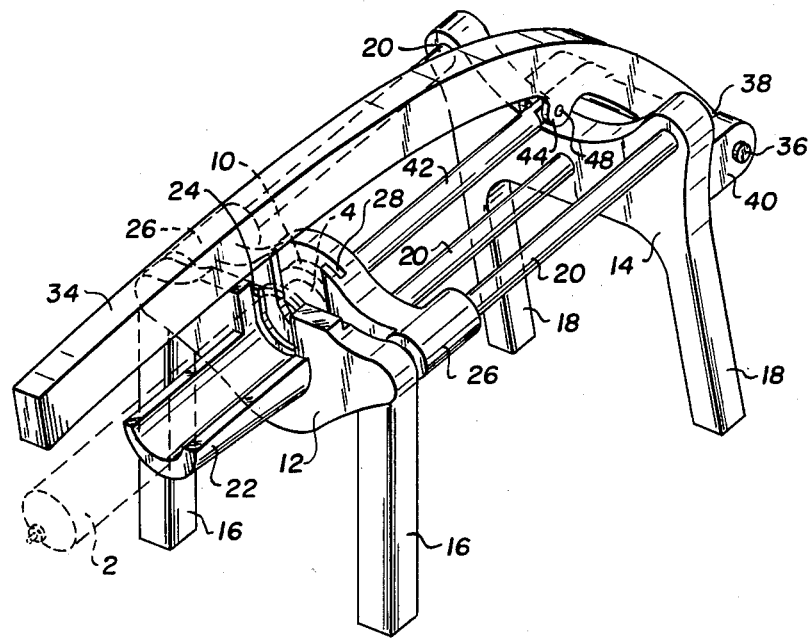
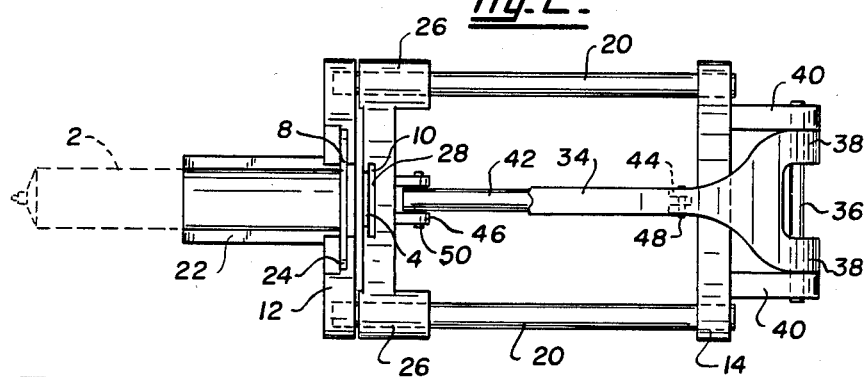
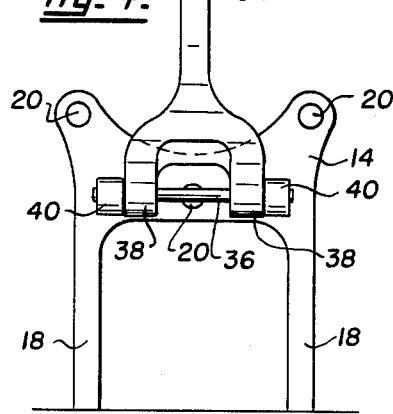
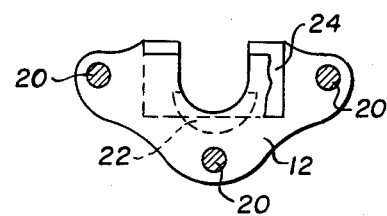

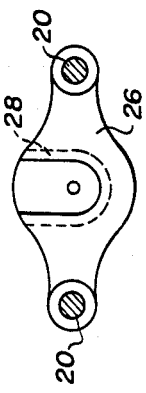
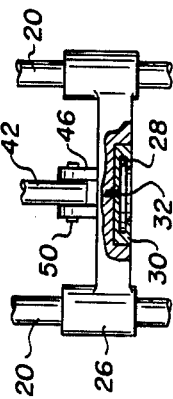
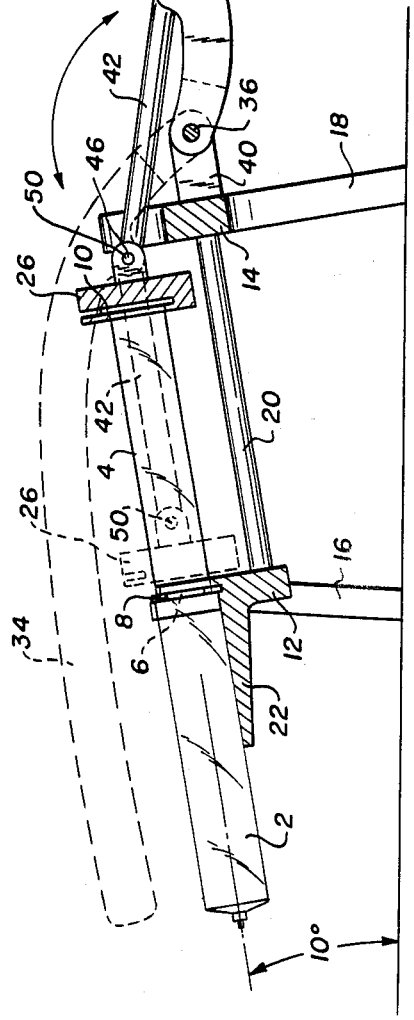

SYRINGE INJECTOR

FIELD OF THE INVENTION

This invention relates to a syringe injector.

DESCRIPTION OF THE PRIOR ART

The administration of injections by syringe is, of course, of considerable antiquity. The liquid is injected into the patient, typically into a vein, through a needle inserted into the patient. The needle is attached to a syringe or to a catheter attached to the syringe. The syringe is, in effect, simply a piston acting in a cylinder and communicating with the hollow needle.

A problem arises when the liquid to be injected is viscous and this is a particular problem with x-ray contrast agents. An x-ray contrast agent is a material that is relatively opaque to x-rays so that its presence can clearly be seen on an x-ray photograph of a patient.

The problem is that a viscous liquid must be injected through what is required to be a small diameter needle, bearing in mind that the smaller the needle the less the discomfort for the patient. As a result considerable effort is required to force the viscous liquid from the syringe. There is no satisfactory manual injector that offers assistance in this task. At the moment it is simply required that a larger needle be used or that the injection be administered slowly.

The prior art known to applicant includes U.S. Pat. Nos. 3,819,091 to Hollender; 3,051,172 to Bruchhaus; and 4,444,560 to Jacklich. Although these earlier patents disclose syringe holding devices they do not show a device useful in the environment of the present invention in that, in particular, they do not show the necessary mechanical advantage combined with the ability to inject rapidly large volumes of contrast medium that is an important feature of the present invention.

SUMMARY OF THE INVENTION

Accordingly the present invention seeks to provide a solution to the problem by offering a syringe injector able to provide a mechanical advantage in the administration of an injection.

Accordingly the present invention is a syringe injector to hold a syringe that comprises a barrel and a plunger, the plunger including a rubber piston seal received in the barrel, the injector comprising a support frame; a cradle to receive the syringe barrel at one end of the support frame; holding means to hold the plunger; a lever pivotally attached to the frame; a connecting rod extending from the lever to the holding means; whereby in use, movement of the lever moves the plunger of the syringe and affords mechanical advantage to the user.

In a preferred embodiment the support frame comprises first and second spaced end members, each formed with legs, with the first support member being at said one end of the support frame.

These legs are preferably dimensioned so that on a level surface the frame is inclined downwardly towards the first end, thus ensuring that air bubbles move away from the syringe needle.

DRAWINGS

Aspects of the invention are illustrated, merely by way of example, in the accompanying drawings in which:

FIG. 1 is an isometric view of an embodiment of the present invention;

FIG. 2 is a plan view of the embodiment of FIG. 1;

FIG. 3 is a detail of the embodiment of FIGS. 1 and 2;

FIG. 4 is a rear view of the embodiment of FIGS. 1 and 2;

FIG. 5 is a detail of the embodiment;

FIG. 6 is a further detail;

FIG. 7 is a side elevation illustrating operation of the device;

DESCRIPTION OF THE PREFERRED EMBODIMENTS

Figure 9:
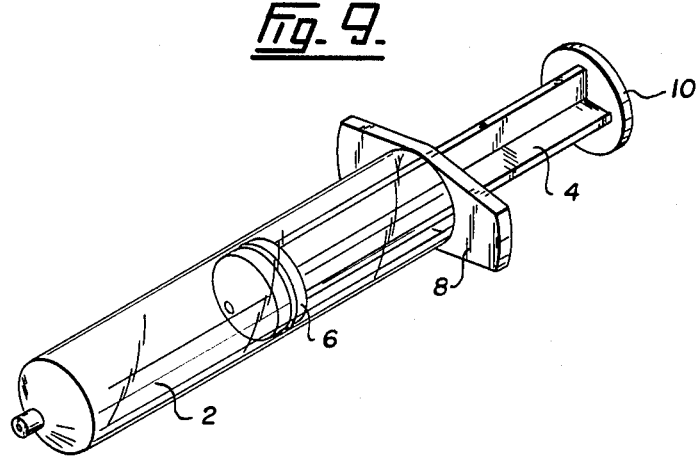
FIG. 9 shows a typical disposable syringe, not forming part of the invention.

The drawings show a syringe injector to hold a syringe comprising, as shown in FIG. 9, a barrel 2 and a plunger 4 with the plunger including a rubber piston seal 6 received in the barrel 2. The syringe is thus entirely conventional and, typically, will be a plastic, disposable syringe that is meant for one use. Typically it will include hubs 8 formed on the syringe barrel 2 and a syringe handle 10 formed on the plunger 4.

The holder comprises a support frame comprising a first member 12 and a second member 14, each formed with legs 16 and 18 respectively. As shown particularly in FIG. 7 legs 16 and 18 are arranged so that the support frame, and thus the syringe when the apparatus is in use, extend downwardly towards the first member 12 at an angle of about 10°.

The first and second end members 12 and 14 are joined by longitudinal members 20. A cradle 22 shaped to receive the syringe barrel 2 extends forwardly from the first support member 12. The first support member 12 includes means to prevent movement of the syringe barrel 2 longitudinally of the holder and, as shown particularly in FIGS. 1, 2 and 3, that means comprises a recess 24 to engage hubs 8 formed on the syringe barrel 2. In enclosing the hubs 8 the recess 24 ensures that the syringe barrel 2 cannot move longitudinally of the holder, regardless of the longitudinal force applied to the syringe barrel 2 through the plunger 4.

If syringe designs change in the future the dimensions of support member 12 may have to be changed to accommodate their design changes.

There are holding means to hold the plunger 4. In the illustrated embodiment the holding means for the plunger 4 comprises a slidable member 26 mounted on, and reciprocable on the side longitudinal members 20 of the frame. The slidable member 26 includes a recess 28 to receive syringe handle 10 formed on the plunger 4. This arrangement is shown in FIGS. 5 and 6 but also in FIGS. 1, 2 and 7. As shown particularly in FIG. 6 the slidable member 26 may be provided with a detachable insert 30, attachable by screw 32, and variable to accommodate different syringe handle sizes.

There is a lever 34 pivotally attached to the second support member 14 by pivot pin 36 extending through hub 38 of the lever 34 and through openings formed in lugs 40 extending from the second support member 14. The pivot pin 36 engaged in the lugs 40 provides the necessary fulcrum for the lever 34.

A connecting rod 42 is pivotally attached to the lever 34 at 44 and extends from the lever 34 to the slidable member 26 where it is pivotally attached at 46. Pivot pins 48 and 50 are used to provide the necessary pivotal joints.

To use the apparatus of FIGS. 1 to 7 the syringe is preferably filled in conventional manner from a container of the necessary x-ray contrast medium. Air is expelled, in conventional manner, and the syringe then placed in the holder with the lever 34 extended as shown in FIG. 7. A connecting catheter joins a needle in the patient's vein to the disposable syringe in the injector. The x-ray contrast medium is expelled by pulling the lever forwardly from the position shown in FIG. 7 to the position shown in FIG. 1. The substantial mechanical advantage provided greatly facilitates the injection of the contrast medium. Typically a 4 or 5 to 1 mechanical advantage is provided. In the embodiment of FIGS. 1 to 7 a positive and negative pressure can be applied to the plunger of the syringe. Negative pressure may be necessary to determine that the needle, not shown in the drawings, is properly inserted into a vein. The angling of the syringe at 10° allows trapped air that may be present to rise.

The mechanical advantage allows the routine use of 21 gauge needles even with high viscosity agents. In patients with small or poor veins the physician may be forced to use a smaller needle, for example 23 gauge, but with the holder according to the present invention a reasonable rate of injection can still be obtained.

Greater ease of injection allows the physician to concentrate on the injection site and the patient's condition rather than on the mechanics of injecting the contrast medium. The device is relatively inexpensive, unlike the sophisticated, expensive angiographic injectors that are sometimes used. Furthermore the simplicity of the device helps to ensure a patient's safety and the design of the device easily permits a robust, yet lightweight structure, not susceptible to mechanical breakdown.

The newer contrast media have a higher viscosity yet the present invention permits the injection of large volumes of relatively viscous contrast media safely and rapidly.

Figure 8:
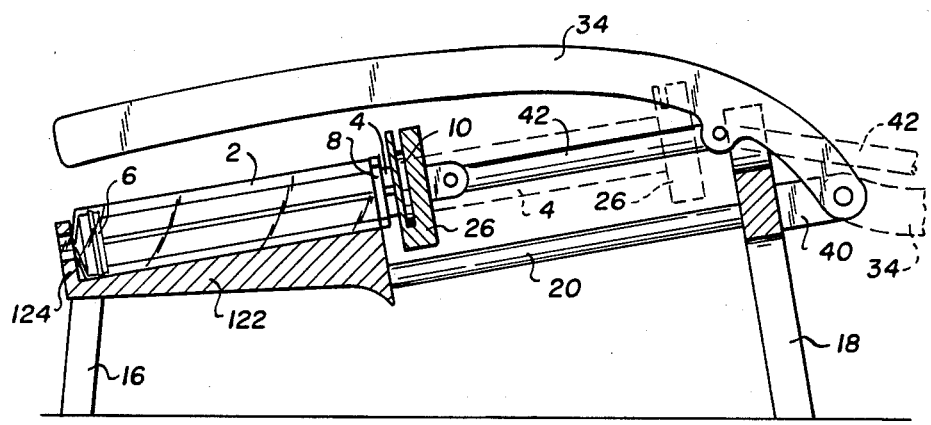
FIG. 8 is a side elevation of a second embodiment.

FIG. 8 shows a second embodiment of the present invention. Where appropriate, the same reference numerals are used for those parts already discussed with regard to FIGS. 1 to 7. However in FIG. 8 cradle 122 has a forward abutment 124 and front legs 16 extending downwardly from the front of cradle 122. That is the recess 24 to engage the hubs 8 is not present. The FIG. 8 embodiment operates as the embodiment of FIGS. 1 to 7 except that it cannot apply negative pressure unless the physician applies hand-pressure to the barrel 2 to prevent backward movement of the barrel 2 with backward movement of the plunger 4. Otherwise all the advantages of the FIGS. 1 to 7 embodiment are present.

We claim:

1. A syringe injector to hold a syringe that comprises a barrel and a plunger, the plunger including a rubber piston seal received in the barrel, hubs adjacent one end of the barrel and a handle extending outwardly from the end of the plunger remote from the piston seal, the injector comprising;
   a support frame;
   a cradle to receive the syringe barrel at one end of the support frame and means to prevent movement of the syringe barrel longitudinally of the cradle;
   holding means to hold the plunger, including a recess to receive the handle of the plunger;
   a primary lever pivotally attached to the frame to pivot in a plane generally perpendicular to the plane of the cradle from a start position extending away from the frame to a finish position overlying the frame;
   a connecting rod extending from the lever to the holding means and longitudinally reciprocable with movement of the lever;
   whereby, in use, movement of the lever moves the connecting rod, the holding means and the plunger of the syringe and affords mechanical advantage to the user.

2. An injector as claimed in claim 1 in which the support frame comprises first and second spaced end members, each formed with legs, the first end member being at said one end of the support frame.

3. An injector as claimed in claim 2 in which the legs are dimensioned so that on a level surface the frame is inclined downwardly towards the first end member.

4. An injector as claimed in claim 2 in which the frame includes longitudinal members joining the first and second end members.

5. An injector as claimed in claim 2 in which the cradle extends forwardly from the first end member.

6. An injector as claimed in claim 1 in which the means to prevent movement of the syringe barrel comprises a recess to engage the hubs formed on the syringe barrel.

7. An injector as claimed in claim 4 in which the holding means to hold the plunger comprises a slidable member mounted on, and reciprocable on, the longitudinal members of the frame.

8. An injector as claimed in claim 7 in which the slidable member includes a recess to receive the syringe handle formed on the plunger.

9. An injector as claimed in claim 6 in which the lever is pivotally mounted on the second support member.

10. An injector as claimed in claim 9 including lugs on the second support member to provide a fulcrum for the lever.

11. An injector as claimed in claim 1 in which the connecting rod is pivotally attached to the lever and the holding means.

* * * * *